(12) United States Patent
Williams et al.

(10) Patent No.: US 6,436,256 B1
(45) Date of Patent: Aug. 20, 2002

(54) ELECTRODES FOR THE MEASUREMENT OF ANALYTES IN SMALL SAMPLE VOLUMES

(75) Inventors: Stephen Charles Williams, Half Moon Bay, CA (US); Bernadette Yon-Hin; Neil Blair, both of Cambridge (GB)

(73) Assignee: Cambridge Sensors Limited (GB)

(*) Notice: Subject to any disclaimer, the term of this patent is extended or adjusted under 35 U.S.C. 154(b) by 0 days.

(21) Appl. No.: 09/445,154

(22) PCT Filed: Jun. 3, 1998

(86) PCT No.: PCT/GB98/01624
§ 371 (c)(1), (2), (4) Date: Mar. 6, 2000

(87) PCT Pub. No.: WO98/55856
PCT Pub. Date: Dec. 10, 1998

(30) Foreign Application Priority Data

Jun. 4, 1997 (GB) .............................................. 9711395

(51) Int. Cl.⁷ .............................................. G01N 27/327
(52) U.S. Cl. ............................. 204/403.06; 204/403.05; 204/403.1
(58) Field of Search ............................. 204/403, 403.5, 204/403.06, 403.1; 205/777.5

(56) References Cited

U.S. PATENT DOCUMENTS

| | | |
|---|---|---|
| 5,141,868 A | 8/1992 | Shanks et al. |
| 5,429,735 A | 7/1995 | Johnson et al. |
| 5,628,890 A | 5/1997 | Carter et al. |
| 5,770,028 A * | 6/1998 | Maley et al. ............... 204/435 |
| 5,820,551 A * | 10/1998 | Hill et al. .................... 204/403 |
| 6,248,596 B1 * | 6/2001 | Durst et al. ................. 436/518 |

FOREIGN PATENT DOCUMENTS

| | | |
|---|---|---|
| EP | 0095946 A1 | 12/1983 |
| EP | 0170375 B1 | 2/1986 |
| EP | 0215446 A2 | 3/1987 |
| EP | 0271102 A2 | 6/1988 |
| EP | 0593096 A2 | 4/1994 |
| WO | WO 92/14836 | 9/1992 |
| WO | WO 97/30344 | 8/1997 |

* cited by examiner

Primary Examiner—Robert J. Warden, Sr.
Assistant Examiner—Kaj K. Olsen
(74) Attorney, Agent, or Firm—Ohlandt, Greeley, Ruggiero & Perle, LLP; George W. Rauchfuss, Jr.

(57) ABSTRACT

A device, for use in the electrochemical analysis of an analyte in a small volume liquid sample, having a non-conducting substrate (1); a conductive layer, deposited on the substrate, in two parts (2a, 2b), defining a non-conducting gap (8) therebetween; an analyte-specific reagent (5) coated on the conductive layer, on one side of the gap; a reference electrode (3) on the conductive layer, on the other side of the gap; a spacer layer (4) deposited over the conductive layer; a monofilament mesh (6) coated with a surfactant or chaotropic agent, the mesh being laid over the reagent, the reference electrode and the spacer layer; and a second non-conductive layer (7) adhered to the mesh layer, but not coextensive therewith, thereby providing a sample application area (9) on the mesh.

11 Claims, 1 Drawing Sheet

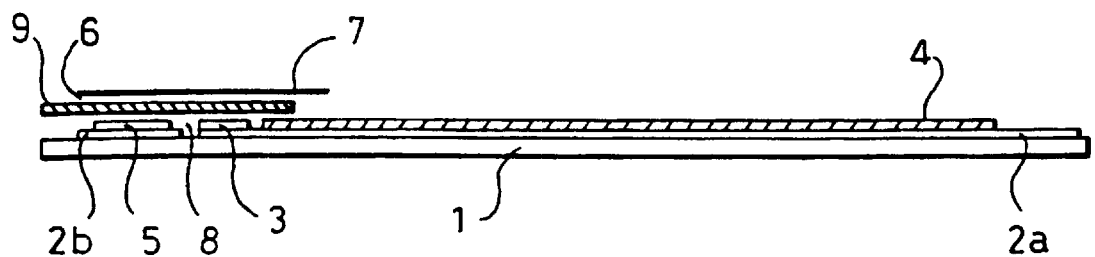
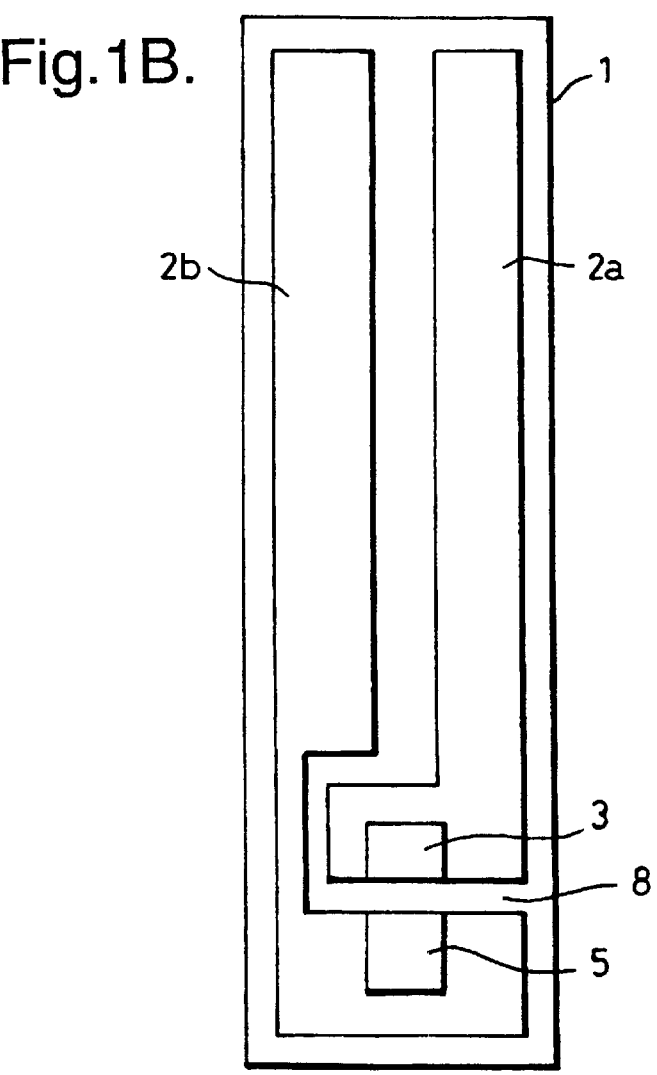

ELECTRODES FOR THE MEASUREMENT OF ANALYTES IN SMALL SAMPLE VOLUMES

FIELD OF THE INVENTION

This invention relates to electrode devices which are capable of accepting small volumes of samples, and to their use in a test method for the detection and quantification of a test species present in a small sample volume.

BACKGROUND OF THE INVENTION

Many devices have been disclosed, that are capable of accepting small volumes of sample material, and that allow analytes present in the sample to be interrogated, either by optical or electrical analytical processes. In particular, the use and construction of sample chambers capable of filling by capillary action has been described in both the patent and scientific literature. See, for example, EP-A-0170375 and US-A-5141868.

Such known devices may comprise electrodes deposited on a non-conducting substrate, coated with a reagent system specific for the analyte of interest and housed within a cavity whose dimensions are sufficiently small to allow introduction of a sample by capillary action. The sample is retained in close proximity to the electrodes, and the electrodes are configured in such a way as to facilitate the measurement of specific electrical properties of the sample.

Such devices suffer from numerous drawbacks, in particular the need to control the dimensions of the cavity within very tightly defined limits. Exceeding these manufacturing tolerances will prevent the sample from entering the cavity by capillary action.

Further, when viscous sample fluids such as blood are introduced into the cavity, the chamber will fill with sample relatively slowly, thus delaying the time taken-to complete the analysis. Variations in sample viscosity and thus sample surface tension characteristics result in variations of the fill time; this not only compromises the overall analysis time but, more importantly, leads to imprecision in the analytical result, since the time over which the sample is exposed to the analyte-specific reagent is subject to variation.

WO-A-9730344 discloses an electrode device which includes a polyester mesh adapted to guide the sample to the reference electrode. This device requires that the reagent includes a filler having both hydrophobic and hydrophilic surface regions, in order to avoid problems associated with variations in sample handling and to be independent of the haemocrit of the sample, for glucose testing.

ACCORDING TO THE INVENTION

According to the present invention, a device which is capable of electrochemical measurement of the levels of analytes present in a small fluid sample volume, comprises a conductive layer coated with an analyte-specific reagent and deposited on a non-conducting substrate, a spacer layer deposited onto the non-conducting substrate by thick film printing, a monofilament mesh material coated with a surfactant and/or a chaotropic reagent, the mesh being overlaid onto the space layer, and a second non-conductive substrate adhered to the mesh layer. The device is thus multilayer in construction, and comprises two surfaces separated by a printed spacer layer and forming a cavity or area which is open at one end for the introduction of sample. This cavity or area is filled with a mesh material that extends beyond the second substrate and forms a sample application area.

A device according to the present invention may be produced and used by the steps of (a) depositing a conducting layer of carbon and graphite, in a polymer binder, on a first non-conducting substrate;

(b) depositing a second conducting layer consisting of silver/silver chloride to function as a reference/counter electrode, adjacent to but not continuous with the first conducting layer;

(c) coating the surface of the first conductive layer with a reagent or mixtures of reagents which react specifically with an analyte or analytes in a sample material;

(d) forming a spacer layer by thick film printing on top of the first non-conducting substrate and on top of the first conducting layer, in order to leave a portion of each of the first and second conducting layers exposed;

(e) locating a coated mesh material on top of the spacer layer and permanently securing it to the spacer layer;

(f) locating a second non-conducting substrate on top of the mesh material and permanently securing it in such a way as to leave an extended area of mesh exposed;

(g) applying a sample to the extended mesh area in order to fill or flood the device sensing area, by wetting of the mesh with sample; and (h) quantifying the analyte in the sample by reaction with the reagent on the first conducting layer.

The electrode device allows the application of a small volume of sample (typically less than 2 $\mu$L) to the mesh extension. This is followed by flooding of the device sensing area with sample, bringing it into intimate contact with the measuring electrodes. The cavity may be filled either by placing a drop of sample liquid on top of the exposed mesh at the edge of the cavity or by contacting the edge of the cavity with the sample.

DESCRIPTION OF THE INVENTION

The accompanying drawings are provided for the purpose of illustration only. In the drawings:

FIG. 1A is a schematic side view of a sensor device embodying the present invention; and FIG. 1B is a plan view of part of the embodiment shown in FIG. 1A.

In more detail, the drawings show a non-conducting sheet 1 and, deposited thereon, a conducting electrode in two parts 2a, 2b. The part 2a carries a reference/counter electrode 3, and the part 2b carries a reagent layer 5. The parts 2a, 2b also carry a spacer layer 4 (this and other components described below are not shown in FIG. 1B, which is provided merely to show the electrical configuration). A mesh material 6 is laid over the electrode 3, the spacer 4 and the reagent layer 5. A tape 7 is provided over the mesh material 6.

A device sensing area 8 is defined between the respective parts of the conductive layer and thus between the reagent and the reference electrode. The mesh material is not coextensive with the tape 7, thereby defining a sample application area 9. In use, sample applied to area 9 is carried by the mesh 6, so that it floods areas 3, 5 and 8. The presence of an analyte in the sample can now be determined electrochemically.

DESCRIPTION OF THE INVENTION

The mesh material is interposed between the spacer layer (on the first substrate) and the second substrate, and functions to reduce the surface tension and/or viscosity of the sample, by virtue of the wetting agent coated onto its surface. Application of sample to the extended portion of the mesh, results in dissolution of the mesh coating material into the sample, reducing sample surface tension and allowing sample to flow into the device cavity. Sample will not enter the device cavity in the absence of a wetting reagent coated onto the mesh. Alternatively, in complex samples such as blood, where the measurement of a specific analyte is adversely affected by the presence of whole cells, for example by poisoning an electrode surface, the mesh may be coated with an agent which lyses the cells on contact; this has the added advantage of reducing sample viscosity at the same time, whilst removing the whole cell interference.

The system may be deposited as a single electrode, a micro-electrode or as a microelectrode array. The electrode may be used in conjunction with reference/counter electrodes deposited on the same substrate.

The non-conducting substrate material may be a sheet of, for example, polyester, polycarbonate, polyvinyl chloride, high density polypropylene or low density polypropylene. In a preferred embodiment, a polyester sheet material is heat-stabilised prior to application of the conducting layers, to confer dimensional stability on the polyester material prior to processing.

The conducting layer preferably contains graphite, carbon and a polymer binder. For example, the graphite component has an average particle size of up to 20 $\mu$m, e.g. 1–20 $\mu$m, a typical surface area of up 50 $m^2/g$, e.g. 1–50 $m^2/g$. It is inherently conductive; it may be derived from either natural sources or produced synthetically. The carbon component preferably has an average particle size less than 1 $\mu$m, e.g. 5–70 nm, and a typical surface area of less than 150 $m^2/g$. Like the graphite component, it is also inherently conductive.

The polymer binder may be either thermoset or thermoplastic. It may be derived from any of diverse polymer families, including vinyl chloride, vinyl acetate, vinyl alcohol (and copolymers of vinyl chloride, acetate and alcohol), hydrocarbons, ethyl and methyl celluloses, epoxys, polyesters, alkyds and polymers containing functional reactive groups such as carboxyl, hydroxyl, amine, thiol, ester, epoxide and amide groups, which enable the polymer to be cross-linked.

The conducting electrode material may be deposited on the non-conducting substrate by a conventional printing process, e.g. thick film printing (also known as screen printing), lithography, letterpress printing, vapour deposition, spray coating, ink jet printing, laser jet printing, roller coating or vacuum deposition. Following deposition of the conductive electrode material, the polymer binder may be stabilised or cured by a number of conventional processes, including forced air drying, forced air drying at elevated temperatures, infra-red irradiation, ultraviolet irradiation, ion beam irradiation or gamma irradiation. All of these processes result to varying degrees in the cross-linking of individual molecules of the polymer binder. The use of ultraviolet radiation requires the inclusion of a photo-sensitising reagent in the conductive electrode material, to initiate the polymer cross-linking reaction.

The reagent located on top of the first conductive layer is characterised in that it contains all the components in a solid state necessary for measuring the concentration of analyte in a sample. Such components include enzymes, enzyme cofactors, coenzymes, co-substrates, antibodies or other analyte-binding partners, DNA or RNA, redox partners, buffers, ionophores and salts.

The reagent may also support matrices, binders and stabilisers for the other components. For example, suitable matrices include particles of graphite, carbon, silica, glass, latex or polyvinyl chloride. Suitable binders include polyvinyl alcohol, polyvinyl acetate, polyvinyl pyrrolidine, proteins, cellulose and cellulose acetate. Suitable stabilisers include alcohols, esters, proteins, protein hydrolysates and both simple and complex carbohydrates.

The reagent may comprise a number of individually applied layers, each containing specific components. Its composition is such that it undergoes at least partial dissolution when contacted by the fluid sample.

The reagent may be deposited on the first conducting layer by a conventional deposition process, e.g. thick film printing (also known as screen printing), lithography, letter press printing, vapour deposition, spray coating, ink jet printing, laser jet printing, roller coating or vacuum deposition. Combinations of these deposition processes may be used to construct a multilayer. Following deposition of the reagent (or after deposition of each individual layer), the layer may be stabilised or cured by a number of conventional processes, including those described above, in order to achieve cross-linking of individual molecules of the polymer binder.

The spacer layer may be deposited on the first non-conducting substrate by conventional thick film deposition, and may be stabilised or cured by a number of conventional processes, including those described above, in order to cross-link individual molecules of the polymer binder. The thickness of the spacer layer may be controlled by means of a number of parameters, including printing conditions (pressure, speed, screen tension and emulsion thickness) and ink properties such as solids content and viscosity.

The mesh layer is preferably a synthetic, monofilament, woven material. It may be made from polyester or nylon. The mesh is coated with a surfactant material, a detergent or wetting or lysing agent. Examples include fluorosurfactants, non-ionic surfactants, ionic surfactants, zwitterionic surfactants, saponin and sodium cholate.

Electrodes of the invention have several desirable characteristics. For example, the devices require a very small volume, typically less than 2 $\mu$L, of sample such as whole blood, plasma, serum, interstitial fluid, sweat or saliva. When the sample fills the sample cavity, a very thin film of sample is spread across the surface of the deposited reagent, maximising contact with the reagent, and enabling reagent to be dissolved in the sample rapidly. This allows rapid attainment of the steady state.

In a preferred embodiment of the device, the cavity is positioned at the end of edge of the device. This device may be readily filled with sample by contacting the edge of the test strip with the sample. In another preferred embodiment, the cavity may be positioned 0–2 mm from the edge of the device, thus exposing an area of the test strip which may be scraped along a surface (such as a punctured area of skin), in order to collect the sample.

Electrodes of the invention may be used for the analysis of analytes/species which can be directly oxidised or reduced by the removal or addition of electrons at an electrode; analytes/species which can be readily converted, by an enzyme or a series of enzymes, to a product which can be directly oxidised or reduced by the removal or addition of electrons at an electrode; analytes/species which can be converted to a product by an enzyme, with the concomitant oxidation or reduction of an enzyme cofactor, wherein the cofactor may then be directly oxidised or reduced by the addition/removal of electrons; and analytes/species which can be converted to a product by an enzyme which is in intimate contact with the electrode surface, such that the enzyme is able to pass or receive electrons directly from the electrode. The novel device is particularly suitable for use as a glucose sensor. In this case, the reagent is preferably glucose dehydrogenase; this can provide a glucose reading that is substantially independent of the haemocrit of the sample.

The following Example illustrates the invention.

EXAMPLE

A conductive ink material is printed onto a non-conducting polyester sheet material (125 µm thick) by a screen printing process. The conductive ink material consists of a mixture of graphite particles (average particle size 1 µm, with a surface area of 15 m$^2$/g), conductive carbon particles (average particle size 40 nm, surface area 100 m$^2$/g), and a vinyl chloride/acetate copolymer binder in an organic solvent. After deposition of the conductive ink, solvents are removed in a forced air oven, whilst the application of elevated temperature initiates the chemical cross-linking of polymer binder by the bifunctional amine.

A silver/silver chloride, screen-printed reference/counter electrode is located adjacent to the conductive carbon layer on the polyester support. A spacer layer is then screen-printed in such a way as to leave part of the conductive carbon electrode and all of the reference/counter electrode exposed.

A multilayer reagent mixture, specific for the measurement of glucose, is prepared. It comprises 2,6-dichlorophenolindophenol, Nile Blue, Medola Blue or any other suitable mediator for the enzyme cofactor NADH, deposited onto the exposed conductive carbon/graphite layer from aqueous solution by pipetting, and dried to leave a film of mediator coated onto the conductive carbon/graphite layer. A second layer is deposited by thick film printing, consisting of a mixture of graphite, NAD$^+$, buffer salts, surfactants, stabilisers and rheology modifiers. This is then dried. A third layer is deposited by pipetting, consisting of an aqueous solution of glucose dehydrogenase (NAD-dependent), buffer salts and stabilisers. That is then also dried.

A surfactant-coated monofilament mesh material is located on top of the spacer layer and secured by thick film deposition of a second spacer layer. A second non-conducting layer, comprising a 75 µm thick polyester tape material coated on one side with a pressure-sensitive adhesive, is positioned on top of the monofilament mesh in such a way as to leave an extended area of the mesh exposed. The exposed area acts as a sample application zone.

When a suitable potential difference is applied between the conductive carbon and the silver chloride reference electrodes, the electrode device can be used for the measurement of glucose in a sample of blood, using standard electrochemical techniques such as chronoamperometry. Glucose is converted to gluconolactone, with concomitant conversion of NAD+to NADH by the action of the NAD$^+$-dependent glucose dehydrogenase, and NADH is reoxidised to NAD$^+$ by the mediator compound. The mediator compound is in turn reoxidised at the electrode surface, and the current produced is proportional to the concentration of glucose in the sample.

What is claimed is:

1. A device for use in the electrochemical analysis of an analyte in a liquid sample, which comprises:

a non-conducting substrate;
    a discontinuous conductive layer deposited on adjacent first and second portions, respectively, of the non-conducting substrate and defining a non-conducting gap between the first and second portions;
    an analyte-specific reagent coated on the conductive layer on the first portion;
    a reference electrode on the the conductive layer on the second portion;
    a spacer layer deposited over the conductive layer;
    a monofilament mesh coated with a surfactant or chaotropic agent, the mesh being laid over the analyte-specific reagent, the reference electrode and the spacer layer; and
    a second non-conductive layer, adhered to and covering the mesh layer, said second non-conducting layer having an exterior edge such that the second non-conducting layer is not co-extensive with the mesh layer, thereby providing an exposed portion of the mesh at one exterior edge of the mesh.

2. A device according to claim 1, wherein the reagent does not contain filler having both hydrophobic and hydrophilic surface regions.

3. A device according to claim 2, wherein the analyte is glucose and the reagent is glucose dehydrogenase.

4. A device according to claim 2, wherein the mesh is additionally coated with a cell lytic agent.

5. A device according to claim 2, wherein the first conductive layer comprises graphite particles, carbon particles and a polymer binder, wherein the graphite particles have an average particle size of 1–20 µm and a surface area of 1–50 m$^2$/g, and the carbon particles have an average size of 5–70 nm and a surface area of less than 150 m$^2$/g.

6. A method for the electrochemical analysis of an analyte in a liquid sample, which comprises applying the sample to the application area on a device according to claim 2, and quantifying the analyte by reaction with the reagent.

7. A device according to claim 1, wherein the analyte is glucose and the reagent is glucose dehydrogenase.

8. A device according to claim 1, wherein the mesh is additionally coated with a cell lytic agent.

9. A device according to claim 1, wherein the first conductive layer comprises graphite particles, carbon particles and a polymer binder, wherein the graphite particles have an average particle size of 1–20 µm and a surface area of 1–50 m$^2$/g, and the carbon particles have an average size of 5–70 nm and a surface area of less than 150 m$^2$/g.

10. A method for the electrochemical analysis of an analyte in a liquid sample, which comprises applying the sample to the application area on a device according to claim 1, and quantifying the analyte by reaction with the reagent.

11. A device for use in the electrochemical analysis of an analyte in a liquid sample, which comprises:

a non-conducting substrate;
    a first and a second conductive layer deposited on first and second portions, respectively, of the non-conducting substrate and defining a non-conducting gap between the first and second conductive layers;
    an analyte-specific reagent coated on the first conductive layer;
    a reference electrode on the second conductive layer;
    a spacer layer deposited over a portion of both the first and second conductive layers;
    a monofilament mesh coated with a surfactant or chaotropic agent, the mesh being laid over the analyte-specific reagent, the reference electrode and the spacer layer; and a second non-conductive layer, adhered to and covering the mesh layer, said second non-conducting layer having an exterior edge such that the second non-conducting layer is not co-extensive with the mesh layer, thereby providing an exposed edge portion of the mesh at one exterior edge of the mesh.

* * * * *